United States Patent
Soon-Shiong et al.

(10) Patent No.: US 10,793,875 B2
(45) Date of Patent: Oct. 6, 2020

(54) COMPOSITIONS AND METHODS FOR VIRAL DELIVERY OF NEOEPITOPES AND USES THEREOF

(71) Applicant: Nant Holdings IP, LLC, Culver City, CA (US)

(72) Inventors: Patrick Soon-Shiong, Los Angeles, CA (US); Shahrooz Rabizadeh, Los Angeles, CA (US); Kayvan Niazi, Agoura Hills, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 0 days.

(21) Appl. No.: 16/060,020

(22) PCT Filed: Dec. 7, 2016

(86) PCT No.: PCT/US2016/065412
§ 371 (c)(1),
(2) Date: Jun. 6, 2018

(87) PCT Pub. No.: WO2017/100338
PCT Pub. Date: Jun. 15, 2017

(65) Prior Publication Data
US 2018/0363005 A1 Dec. 20, 2018

Related U.S. Application Data

(60) Provisional application No. 62/263,812, filed on Dec. 7, 2015.

(51) Int. Cl.
| | |
|---|---|
| *C12N 15/86* | (2006.01) |
| *A61K 38/20* | (2006.01) |
| *A61K 39/00* | (2006.01) |
| *A61K 38/19* | (2006.01) |
| *A61K 35/761* | (2015.01) |

(52) U.S. Cl.
CPC ............ *C12N 15/86* (2013.01); *A61K 35/761* (2013.01); *A61K 38/19* (2013.01); *A61K 38/208* (2013.01); *A61K 38/2013* (2013.01); *A61K 38/2046* (2013.01); *A61K 38/2086* (2013.01); *A61K 39/0011* (2013.01); *A61K 2039/5256* (2013.01); *C12N 2710/10021* (2013.01); *C12N 2710/10043* (2013.01); *C12N 2710/10343* (2013.01)

(58) Field of Classification Search
CPC ............ A61K 38/191; A61K 39/0011; A61K 38/208; A61K 38/21; A61K 2039/53; A61K 39/001114; C12N 5/0636; C12N 2501/06; C12N 2501/23; C12N 2502/30; C12N 2510/00; C12N 2710/16134
See application file for complete search history.

(56) References Cited

U.S. PATENT DOCUMENTS

| | | | |
|---|---|---|---|
| 7,473,532 B2 | 1/2009 | Darfler et al. | |
| 2010/0203109 A1 | 8/2010 | Herlyn | |
| 2012/0059670 A1 | 3/2012 | Sanborn et al. | |
| 2012/0066001 A1 | 3/2012 | Sanborn et al. | |
| 2013/0243723 A1* | 9/2013 | Hadden ................ | A61K 38/164 424/85.2 |

FOREIGN PATENT DOCUMENTS

| | | |
|---|---|---|
| AU | 2016366183 B2 | 1/2020 |
| AU | 2019280006 A1 | 1/2020 |
| CA | 3 007 656 A1 | 6/2017 |
| CN | 108603175 A | 9/2018 |
| JP | 2019-500057 A | 1/2019 |
| KR | 10-2019-0019895 A | 2/2019 |
| MX | 2018006996 A | 5/2019 |
| TW | 201725265 A | 7/2017 |
| WO | 2001-95919 A2 | 12/2001 |
| WO | 2002-057290 A2 | 7/2002 |
| WO | 2005/026370 A2 | 3/2005 |
| WO | 2011/119628 A2 | 9/2011 |
| WO | 2011/143656 A2 | 11/2011 |
| WO | 2011/149534 A2 | 12/2011 |
| WO | 2014/039961 A1 | 3/2014 |
| WO | 2014-046983 A1 | 3/2014 |
| WO | 2014/168874 A2 | 10/2014 |
| WO | 2017/100338 A1 | 6/2017 |
| WO | 2017/100338 A4 | 8/2017 |

OTHER PUBLICATIONS

Hacohen et al. Cancer Immunolo Res. 2013 1 (1), pp. 11-15.*
Shi et al. World Journal of Gastroenterology 2003, 9(1), 73-78.*
Kloos, Arnold, et al., "PolySia-Specific Retargeting of Oncolytic Viruses Triggers Tumor-Specific Immune Responses and Facilitates Therapy of Disseminated Lung Cancer," Cancer Immunology Research [e-pub] Feb. 19, 2015, vol. 3, No. 7, pp. 751-763.
ISA/KR, International Search Report and Written Opinion for Int'l Patent Application No. PCT/US2016/065412, dated Apr. 26, 2017, 18 pages.
Morse et al., "Phase I Study of Immunization with Dendritic Cells Modified with Fowlpox Encoding Carcinoembryonic Antigen and Costimulatory Molecules", Clin. Cancer Res., Apr. 2005, vol. 11, No. 8, pp. 3017-3024.
Second Examination Report received for Australian Patent Application No. 2016366183 dated Dec. 4, 2019, 04 pages.
Srivastava Pramod K. "Neoepitopes of Cancers: Looking Back, Looking Ahead", Cancer Immunology Research, 2015, vol. 3, No. 9, pp. 969-977.

(Continued)

*Primary Examiner* — Bao Q Li
(74) *Attorney, Agent, or Firm* — Martin Fessenmaier; Umberg Zipser, LLP (57) ABSTRACT

Cancer immunotherapy is enhanced by co-expression of cancer associated or tumor-specific (neo)epitopes with co-stimulatory molecules and/or other immune activators. Where desired, treatment may be enhanced by administration of a immune checkpoint inhibitor.

22 Claims, 3 Drawing Sheets

Specification includes a Sequence Listing.

(56) References Cited

OTHER PUBLICATIONS

Tsang et al., "Analyses of Recombinant Vaccinia and Fowlpox Vaccine Vectors Expressing Transgenes for Two Human Tumour Antigens and Three Human Costimulatory Molecules", Clinical Cancer Research, 2005, vol. 11, pp. 1597-1607.
First Examination Report received for Australian Patent Application Serial No. 2016366183, dated Apr. 11, 2019, 8 pages.
Notice of Acceptance received for Australian Patent Application Serial No. 2016366183, dated Dec. 19, 2019, 3 pages.
Morse et al., Phase I Study of Immunization with Dendritic Cells Modified with Fowlpox Encoding Carcinoembryonic Antigen and Costimulatory Modecules, Clin. Cancer Res., Apr. 2005, vol. 11, No. 8, pp. 3017-3024.
Second Examination Report received for Australian Patent Application Serial No. 2016366183 dated Dec. 4, 2019, 04 pages.
Piragyte, I. et al., Actin Engine in Immunological Synapse, Immune Network, Jun. 3, 2012, pp. 71-83, vol. 12, No. 3.
Corrales, L., et al., Molecular Pathways: targeting the Stimulator of Interferon Genes (STING) in the Immunotherapy of Cancer, HHS Public Access, Nov. 1, 2015, pp. 4774-4779, 21(21).
First Office Action received for Taiwan Patent Application No. 105140301 dated Jan. 20, 2020, 7 pages.
Vigneron et al., "Database of T cell-defined human tumor antigens: the 2013 update", Cancer Immunity, Jul. 15, 2013, vol. 13, No. 15, pp. 1-6 (Cited from Specification).
Lundegaard et al., "NetMHC-3.0: accurate web accessible predictions of human, mouse and monkey MHC class I affinities for peptides of length 8-11", Nucleic Acids Research, May 7, 2008, vol. 36, pp. W509-W512 (Cited from Specification).
Zhang et al., "Machine learning competition in immunology—Prediction of HLA class I binding peptides", Journal of Immunological Methods, 2011, vol. 374, pp. 1-4 (Cited from Specification).
Li et al., "Dendritic cells derived from pluripotent stem cells: potential of large scale production", World Journal of Stem Cells, Jan. 26, 2014, vol. 6, No. 1, pp. 1-10 (Cited from Specification).
Amalfitano et al., "Production and Characterization of Improved Adenovirus Vectors with the E1, E2b, and E3 Genes Deleted", Journal of Virology, Feb. 1998, vol. 72, No. 2, pp. 926-933 (Cited from Specification).
Niazi et al., "Activation of human CD4+ T cells by targeting MHC class II epitopes to endosomal compartments using human CD1 tail sequences", Immunology, 2007, vol. 122, pp. 522-531 (Cited from Specification).
Extended European Search Report received for European Patent Application Serial No. 16873778.1 dated Apr. 23, 2019, 12 pages.
Lutz et al., "Can We Predict Mutant Neoepitopes in Human Cancers for Patient-Specific Vaccine Therapy?", Cancer Immunology Research, Jun. 2014, vol. 2, No. 6, pp. 518-521.
Fritsch et al., "HLA-binding properties of tumor neoepitopes in humans", Cancer Immunol Research, Jun. 2014, vol. 2, No. 6, 14 pages.
Tagliamonte et al., "Antigen-specific vaccines for cancer treatment", Human Vaccines & Immunotherapeutics, vol. 10, No. 11, 48 pages.
Boegel et al., "A catalog of HLA type, HLA expression, and neoepitope candidates in human cancer cell lines", OncoImmunology, 2014, vol. 3, No. 8, 13 pages.
Tureci et al., "Targeting the Heterogeneity of Cancer with Individualized Neoepitope Vaccines", Clinical Cancer Research, 2016, vol. 22, No. 8, pp. 1885-1896.
Carapito et al., "Next-Generation Sequencing of the HLA locus: Methods and impacts on HLA typing, population genetics and disease association studies", Human Immunology, 2016, vol. 77, pp. 1016-1023.
Nguyen et al., "Identifying patient-specific neoepitopes for cell-based and vaccine immunotherapy within the Cancer Genome Atlas reveals rarely shared recurrent neoepitopes", Immunotherapy, Nov. 29, 2016, 1 page.
Notice of Office Action Received for Korean Patent Application Serial No. 1020187019236 dated Mar. 31, 2020, 11 pages (Including English translation).
International Preliminary Report on Patentability Chapter II received for PCT Application Serial No. PCT/ US2016/065412 dated Apr. 16, 2018, 33 pages.
Fooksman et al., "Functional Anatomy of T Cell Activation and Synapse Formation", Annu Rev Immunol, Mar. 2010, vol. 28, 30 pages.
Bakdash et al., "The nature of activatory and tolerogenic dendritic cell-derived signal II", Frontiers in Immunology, Feb. 2013, vol. 4, No. 53, pp. 1-18.
Communication pursuant to Article 94(3) EPC received for European Patent Application Serial No. 16873778.1 dated Jun. 22, 2020, 5 pages.
Notice of Final Rejection received in Korean Patent Application Serial No. 1020187019236 dated Jun. 30, 2020, 2 pages (Including English Translation).
Office Action received for Taiwanese Patent Application Serial No. 105140301 dated Jun. 4, 2020, 15 pages (Including English Translation).
Hodge et al., "Harnessing the unique local immunostimulatory properties of modified vaccinia Ankara (MVA) virus to generate superior tumor-specific immune responses and antitumor activity in a diversified prime-and-boost vaccine regimen", Vaccine, Jul. 16, 2009, vol. 27, No. 33, 17 pages.

\* cited by examiner

COMPOSITIONS AND METHODS FOR VIRAL DELIVERY OF NEOEPITOPES AND USES THEREOF

This application claims priority to our U.S. Provisional Application having the Ser. No. 62/263,812, filed Dec. 7, 2015.

FIELD OF THE INVENTION

The field of the invention is treatment of neoplastic diseases, and especially as they relate to prophylaxis and treatment of neoplastic diseases using recombinant viruses.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

It is well known that most, if not all neoplastic diseases are accompanied by a relatively large number of mutations, including point mutations, insertions, deletions, and translocations. Thus, it is reasonable to assume that neoplastic cells should also be characterizable by presence of one or more mutated proteins. Unfortunately, and despite such simple premise, the search for mutated proteins that are suitable for diagnosis and therapy has been complicated by the fact that different cancer types have different mutated proteins, and worse yet, different patients with the same tumor type have vastly different reservoirs of mutated proteins.

More recently, as a result of numerous research efforts, a relatively small collection of T-cell defined human tumor antigens has become available (see e.g., Cancer Immunity (15 Jul. 2013) Vol. 13, p. 15), however, these antigens have not resulted in a single effective therapeutic agent. Moreover, as these antigens were already present in a patient diagnosed with cancer, use of those antigens in immunotherapy is at least conceptionally questionable as these antigens should have given rise to an appropriate immune response. Moreover, even if tumor specific antigens are identified and used in a cancer vaccine, the immune response to such antigens may not be sufficiently strong to elicit a therapeutic effect.

Thus, while at least theoretically all tumor antigens could be identified, identification will fail to provide a meaningful and actionable data set. Therefore, there is not only a need for new systems and methods that allow for rapid identification, diagnostic and/or therapeutic use of cancer neoepitopes, but also a need to elicit a prophylactically and/or therapeutically effective immune response to such antigens.

SUMMARY OF THE INVENTION

The inventors have now discovered that neoepitope-based cancer immunotherapy can be rationally guided by use of an omics analysis that first identifies cancer neoepitopes, then confirms an HLA-type match between the HLA-type of the patient and the neoepitope, and subsequently uses an expression system (typically viral delivery/expression system) that not only delivers the nucleic acids encoding the neoepitopes to the patient's immune competent cells but that also provides co-stimulatory molecules. Additionally, such treatment may also include administration of one or more immune checkpoint inhibitors to further augment or stimulate a robust immune response.

In one aspect of the inventive subject matter, the inventors contemplate a method of generating a recombinant virus that includes one step of identifying a cancer-related neoepitope of a patient, a further step of determining binding of the neoepitope to an HLA-type of the patient, and determining an expression level of the neoepitope, a still further step of selecting at least one co-stimulatory molecule, and a step of genetically modifying a virus to include a nucleic acid encoding the at least one co-stimulatory molecule and the cancer-related neoepitope.

With respect to the virus, it is generally referred that the virus is an adenovirus or a replication deficient virus. Moreover, it is further preferred that the virus is non-immunogenic. Thus, especially preferred viruses include an adenovirus, and especially an Ad5 [E1⁻E2b⁻].

Cancer-related neoepitopes of the patient are preferably identified in silico by location-guided synchronous alignment of omics data of tumor and matched normal samples, and contemplated methods may further comprise a step of predicting the HLA type of the patient in silico. While not limiting to the inventive subject matter, it is preferred that the expression level of the neoepitope is at least 20% compared to a matched normal sample.

It is further contemplated that the co-stimulatory molecule is selected from the group of B7.1 (CD80), B7.2 (CD86), CD30L, CD40, CD40L, CD48, CD70, CD112, CD155, ICOS-L, 4-1BB, GITR-L, LIGHT, TIM3, TIM4, ICAM-1, and LFA3 (CD58). Moreover, the nucleic acid may further include a sequence encoding a cytokine (e.g., IL-2, IL-7, IL-12, IL-15, an IL-15 superagonist (IL-15N72D), and/or an IL-15 superagonist/IL-15RαSushi-Fc fusion complex). Alternatively, or additionally, the nucleic acid further may also include a sequence encoding at least one component of a SMAC (e.g., CD2, CD4, CD8, CD28, Lck, Fyn, LFA-1, CD43, and/or CD45 or their respective binding counterparts). Where desired, the nucleic acid may additionally comprise a sequence encoding an activator of a STING pathway, such as a chimeric protein in which a transmembrane domain of LMP1 of EBV is fused to a signaling domain of IPS-1.

Moreover, it is further contemplated that a segment may be included into the nucleic acid that encodes at least a second (or third, or fourth, etc.) distinct cancer-related neoepitope. So generated recombinant viruses may then be cultured to obtain at least $10^4$ or more typically $10^7$ virus particles.

Consequently, the inventors also contemplate a recombinant virus that comprises a nucleic acid encoding one or more HLA-matched cancer neoepitopes and one or more co-stimulatory molecules functionally coupled to a promoter for expressing the neoepitope and the co-stimulatory molecule in a cell infected with the recombinant virus. Preferably, the virus is an adenovirus and most preferably an Ad5 [E1⁻E2b⁻].

In some aspects of the inventive subject matter, the co-stimulatory molecule is selected from the group of B7.1 (CD80), B7.2 (CD86), CD30L, CD40, CD40L, CD48, CD70, CD112, CD155, ICOS-L, 4-1BB, GITR-L, LIGHT, TIM3, TIM4, ICAM-1, and LFA3 (CD58). Additionally, the nucleic acid in contemplated viruses may further include a sequence encoding a cytokine (e.g., IL-2, IL-7, IL-12, IL-15, an IL-15 superagonist (IL-15N72D), and/or an IL-15 superagonist/IL-15RαSushi-Fc fusion complex), a sequence encoding at least one component of a SMAC (e.g., CD2, CD4, CD8, CD28, Lck, Fyn, LFA-1, CD43, and/or CD45 or their respective binding counterparts), and/or a sequence encoding an activator of a STING pathway (e.g., chimeric protein in which a transmembrane domain of LMP1 of EBV is fused to a signaling domain of IPS-1).

In still further contemplated aspects, pharmaceutical compositions comprising one or more (possibly distinct) recombinant virus presented herein are contemplated. Among other uses, it is generally contemplated that the recombinant virus as presented herein is used in the treatment of a cancer of a patient.

Therefore, the inventors also contemplate a method of treating a patient that includes a step of obtaining a tumor sample and a matched normal sample from the patient, another step of identifying an HLA-type of the patient and identifying a cancer-related neoepitope of the patient, a further step of genetically modifying a virus to include (i) a nucleic acid encoding the neoepitope when the binding affinity is below a predetermined threshold value, and (ii) a nucleic acid encoding at least one co-stimulatory molecule, and a step of administering or causing to administer the genetically modified virus to the patient (e.g., via subcutaneous or intratumoral injection).

In some aspects, the steps of identifying the HLA-type and identifying the cancer-related neoepitope of the patient is performed in silico using genomic information from the tumor sample and the matched normal sample. With respect to suitable co-stimulatory molecules, cytokines, components of a SMAC, and activators of a STING pathway, the same considerations as discussed above apply. Likewise, preferred viruses for administration include an adenovirus, and especially Ad5 [E1⁻E2b⁻]. Where desired, contemplated methods may further include a step of administering an immune checkpoint inhibitor.

Various objects, features, aspects and advantages of the inventive subject matter will become more apparent from the following detailed description of preferred embodiments, along with the accompanying drawing figures in which like numerals represent like components.

DETAILED DESCRIPTION

The inventors have now discovered that efficacy of immunotherapeutic compositions can be improved by targeting patient-specific HLA-matched neoepitopes together with co-delivery of co-stimulatory molecules, preferably using a non- or low-immunogenic viral delivery vector. Co-delivery in preferred aspects may be achieved by mono-, bi, or multi-cistronic expression of the neoantigen(s) and the co-stimulatory molecules from single recombinant delivery system.

To that end, various systems, compositions, and methods of immunotherapy are presented in which a viral vector or other expression system is employed to deliver one or more patient- and disease-specific antigens (e.g., neoepitope, cancer-specific antigen such as PSA, PSMA, etc., or cancer-associated antigen such as brachyury, CEACAM, etc.) to an individual affected with cancer to produce a therapeutic effect that is further enhanced by co-expression of one or more co-stimulatory molecules in the same cell. While not wishing to be bound by a specific theory or hypothesis, the inventors contemplate that the co-expression of the co-stimulatory molecules will assist in formation and maintenance of an immune synapse between an antigen presenting cell and a T-cell for a duration sufficient to activate the T-cell. Therefore, it is contemplated that the therapeutic effect is a protective immune response against cancer cells carrying the antigen.

In one especially contemplated aspect of the inventive subject matter, as discussed in more detail below, patient- and cancer-specific neoepitopes of an individual diagnosed with cancer are determined, preferably using nucleic acid sequence information from tumor and matched normal (i.e., non-cancer) tissue samples of the patient. In this context, it should be appreciated that where neoepitopes are identified using tumor and matched normal samples, all or almost all of otherwise observed non-tumor related changes between a patient sample and a reference genome are excluded. Consequently, and viewed from a different perspective, a comparison between tumor and matched normal samples of the same patient will eliminate all interpersonal or patient-to-reference variations that otherwise occur at relatively high frequency, and as such will eliminate a large quantity of potentially false positive neoepitopes.

Additionally, to increase the likelihood of proper presentation and recognition of the so identified patient- and cancer-specific neoepitopes, the particular HLA-type of the patient is determined (e.g., using in silico prediction as described in more detail below), and binding affinity of the identified neoepitopes is tested in silico to the determined HLA-type. Most typically, the HLA-type determination includes at least three MHC-I sub-types (e.g., HLA-A, HLA-B, HLA-C) and at least three MHC-II sub-types (e.g., HLA-DP, HLA-DQ, HLA-DR), preferably with each sub-type being determined to at least 4-digit depth. Sequences for thusly identified high affinity binders are then back-translated into respective corresponding nucleic acid sequences that are then cloned into a recombinant expression system (e.g., Adenovirus Ad5 [E1⁻E2b⁻]) under the control of one or more regulatory sequences for expression in the host cell after infection with the virus. Still further, it should be appreciated that preferred expression systems will also include one or more sequence elements in connection with the neoepitope sequence(s) that will direct the expressed neoepitope(s) towards the MHC-I and/or MHC-II sub-type to which they have high affinity.

Thus, it is expected that the recombinant virus or other expression system will lead to intracellular expression of true patient- and cancer-specific neoepitopes that are not only suitable for, but also directed towards HLA-presentation that was established to have a high affinity towards the neoepitope, which in turn is expected to generate an immune response with high predictability, leading to a therapeutically effective immune response against the tumor within the host. To even further increase the chances of a therapeutically effective immune response against the tumor, the neoepitopes are co-expressed with one or more co-stimulatory molecules that are required to assemble an activating immune synapse (e.g., ICAM-1, B7.1, CD48 and other SLAM proteins such as CD84, CD150, CD229, and/or CD244) between antigen presenting cells co-expressing antigens and co-stimulatory molecules and T-cells, and/or that are required for T-cell activation (e.g., B7.1 (CD80), B7.2 (CD86), ICAM-1 (CD54), ICOS-L, LFA-3 (CD58), 4-1BBL, CD30L, CD40, CD40L, CD48, CD70, CD112, CD155, GITRL, OX40L, and/or TL1A).

Of course, it should be noted that multiple neoepitopes and co-stimulatory molecules can be used in conjunction with the teachings presented herein, and in especially preferred aspects, at least two, at least three, at least four, or at least five different neoepitopes and at least two, at least three, at least four, or at least five different co-stimulatory molecules will be employed (e.g., encoded in the same recombinant virus, or in distinct viruses). Finally, suitable expression system may further include additional sequences encoding proteins that support an immune response within the cellular environment where the neoepitopes are expressed. For example, suitable proteins include immune stimulatory cytokines (e.g., IL-2, IL-7, IL-12, IL-15, or a IL-15 superagonist, etc.), and/or checkpoint inhibitors (e.g., inhibitors of CTLA-4 or PD1 signaling).

With respect to the recombinant virus or other expression system, it is contemplated that such system is employed to genetically engineer an antigen presenting cell, and especially to transfect a dendritic cell. Alternatively, and as also further described in more detail below, the recombinant virus or other expression system may also be administered as DNA vaccine, or via subcutaneous or intratumoral injection. Similarly, the recombinant virus or other expression system may be used to transfect cells various in vitro that are then administered to the individual.

Choice of Neoepitopes

Neoepitopes can be characterized as expressed random mutations in tumor cells that created unique and tumor specific antigens. Therefore, viewed from a different perspective, neoepitopes may be identified by considering the type (e.g., deletion, insertion, transversion, transition, translocation) and impact of the mutation (e.g., non-sense, missense, frame shift, etc.), which may as such serve as a first content filter through which silent and other non-relevant (e.g., non-expressed) mutations are eliminated. It should further be appreciated that neoepitope sequences can be defined as sequence stretches with relatively short length (e.g., 7-11 mers) wherein such stretches will include the change(s) in the amino acid sequences. Most typically, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is a proteinogenic amino acid and N is a changed amino acid (relative to wild type or relative to matched normal). For example, neoepitope sequences as contemplated herein include sequence stretches with relatively short length (e.g., 5-30 mers, more typically 7-11 mers, or 12-25 mers) wherein such stretches include the change(s) in the amino acid sequences.

Thus, it should be appreciated that a single amino acid change may be presented in numerous neoepitope sequences that include the changed amino acid, depending on the position of the changed amino acid. Advantageously, such sequence variability allows for multiple choices of neoepitopes and so increases the number of potentially useful targets that can then be selected on the basis of one or more desirable traits (e.g., highest affinity to a patient HLA-type, highest structural stability, etc.). Most typically, neoepitopes will be calculated to have a length of between 2-50 amino acids, more typically between 5-30 amino acids, and most typically between 9-15 amino acids, with a changed amino acid preferably centrally located or otherwise situated in a manner that improves its binding to MHC. For example, where the epitope is to be presented by the MHC-I complex, a typical neoepitope length will be about 8-11 amino acids, while the typical neoepitope length for presentation via MHC-II complex will have a length of about 13-17 amino acids. As will be readily appreciated, since the position of the changed amino acid in the neoepitope may be other than central, the actual peptide sequence and with that actual topology of the neoepitope may vary considerably.

Of course, it should be appreciated that the identification or discovery of neoepitopes may start with a variety of biological materials, including fresh biopsies, frozen or otherwise preserved tissue or cell samples, circulating tumor cells, exosomes, various body fluids (and especially blood), etc. Therefore, suitable methods of omics analysis include nucleic acid sequencing, and particularly NGS methods operating on DNA (e.g., Illumina sequencing, ion torrent sequencing, 454 pyrosequencing, nanopore sequencing, etc.), RNA sequencing (e.g., RNAseq, reverse transcription based sequencing, etc.), and protein sequencing or mass spectroscopy based sequencing (e.g., SRM, MRM, CRM, etc.).

As such, and particularly for nucleic acid based sequencing, it should be particularly recognized that high-throughput genome sequencing of a tumor tissue will allow for rapid identification of neoepitopes. However, it must be appreciated that where the so obtained sequence information is compared against a standard reference, the normally occurring inter-patient variation (e.g., due to SNPs, short indels, different number of repeats, etc.) as well as heterozygosity will result in a relatively large number of potential false positive neoepitopes. Consequently, many of the identified neoepitopes will not be likely candidates for successful immunization strategies. Notably, such inaccuracies can be eliminated where a tumor sample of a patient is compared against a matched normal (i.e., non-tumor) sample of the same patient.

In one especially preferred aspect of the inventive subject matter, DNA analysis is performed by whole genome sequencing and/or exome sequencing (typically at a coverage depth of at least 10×, more typically at least 20×) of both tumor and matched normal sample. Alternatively, DNA data may also be provided from an already established sequence record (e.g., SAM, BAM, FASTA, FASTQ, or VCF file) from a prior sequence determination. Therefore, data sets may include unprocessed or processed data sets, and exemplary data sets include those having BAMBAM format, SAMBAM format, FASTQ format, or FASTA format. However, it is especially preferred that the data sets are provided in BAMBAM format or as BAMBAM diff objects (see e.g., US2012/0059670A1 and US2012/0066001A1). Moreover, it should be noted that the data sets are reflective of a tumor and a matched normal sample of the same patient to so obtain patient and tumor specific information. Thus, genetic germ line alterations not giving rise to the tumor (e.g., silent mutation, SNP, etc.) can be excluded. Of course, it should be recognized that the tumor sample may be from an initial tumor, from the tumor upon start of treatment, from a recurrent tumor or metastatic site, etc. In most cases, the matched normal sample of the patient may be blood, or non-diseased tissue from the same tissue type as the tumor.

Likewise, the computational analysis of the sequence data may be performed in numerous manners. In most preferred methods, however, analysis is performed in silico by location-guided synchronous alignment of omics data of tumor and matched normal (from healthy tissue of the same patient) samples as, for example, disclosed in US 2012/0059670A1 and US 2012/0066001A1 using BAM files and BAM servers. Such analysis advantageously reduces false positive neoepitopes and significantly reduces demands on memory and computational resources.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

To further facilitate computational analysis and improve the treatment outcome of neoepitope based therapeutics, neoepitope sequences will be confined to relatively small fragments having a minimum size necessary for MHC-I binding (e.g., at least 5-6 amino acids) and a maximum size advantageous for MHC-I binding (e.g., 9-11 amino acids), or to relatively small fragments having a minimum size necessary for MHC-II binding (e.g., at least 12-14 amino acids) and a maximum size advantageous for MHC-II binding (e.g., 19-21 amino acids). Therefore, neoepitopes will typically have a length of between 7-12 amino acids for MHC-I binding and between 14-20 amino acids for MHC-II binding. For example, suitable neoepitopes may have a length of nine amino acids (where they are determined to bind to MHC-I), including the changed amino acid, and a length of 20 amino acids (where they are determined to bind to MHC-II), including the changed amino acid.

Viewed from a different perspective, a patient- and cancer-specific in silico collection of sequences can be established that have a predetermined length of between 5 and 25 amino acids and include at least one changed amino acid. Such collection will typically include for each changed amino acid at least two, at least three, at least four, at least five, or at least six members in which the position of the changed amino acid is not identical. Such collection can then be used for further filtering (e.g., by sub-cellular location, transcription/expression level, MHC-I and/or II affinity, etc.) as is described in more detail below.

For example, and using synchronous location guided analysis to tumor and matched normal sequence data, the inventors previously identified various cancer neoepitopes from a variety of cancers and patients, including the following cancer types: BLCA, BRCA, CESC, COAD, DLBC, GBM, HNSC, KICH, KIRC, KIRP, LAML, LGG, LIHC, LUAD, LUSC, OV, PRAD, READ, SARC, SKCM, STAD, THCA, and UCEC. All neoepitope data can be found in International application PCT/US16/29244, incorporated by reference herein.

Depending on the type and stage of the cancer, it should be noted that the number of neoepitopes may well exceed a number practical for use in immunotherapeutics. Moreover, not all of the so identified neoepitopes will necessarily lead to a therapeutically effective reaction in a patient. Indeed, it is well known in the art that only a fraction of neoepitopes will generate an immune response. To increase the likelihood of a therapeutically desirable response, the neoepitopes can be further filtered. Of course, it should be appreciated that downstream analysis need not take into account silent mutations for the purpose of the methods presented herein. However, preferred mutation analyses will provide in addition to the type of mutation (e.g., deletion, insertion, transversion, transition, translocation) also information of the impact of the mutation (e.g., non-sense, missense, etc.) and may as such serve as a first content filter through which silent mutations are eliminated. For example, neoepitopes can be selected for further consideration where the mutation is a frame-shift, non-sense, and/or missense mutation.

In a further filtering approach, neoepitopes may also be subject to detailed analysis for sub-cellular location parameters. For example, neoepitope sequences may be selected for further consideration if the neoepitopes are identified as having a membrane associated location (e.g., are located at the outside of a cell membrane of a cell) and/or if an in silico structural calculation confirms that the neoepitope is likely to be solvent exposed, or presents a structurally stable epitope (e.g., *J Exp Med* 2014), etc.

With respect to filtering neoepitopes, it is generally contemplated that neoepitopes are especially suitable for use herein where omics (or other) analysis reveals that the neoepitope is actually expressed. Identification of expression and expression level of a neoepitope can be performed in all manners known in the art and preferred methods include quantitative RNA (hnRNA or mRNA) analysis and/or quantitative proteomics analysis. Most typically, the threshold level for inclusion of neoepitopes will be an expression level of at least 20%, and more typically at least 50% of expression level of the corresponding matched normal sequence, thus ensuring that the (neo)epitope is at least potentially 'visible' to the immune system. In this context, the expression level of the neoepitope is relative to the expression level of the corresponding ('wild type', matched normal) sequence without the neoepitope. Consequently, it is generally preferred that the omics analysis also includes an analysis of gene expression (transcriptomic analysis) to so help identify the level of expression for the gene with a mutation.

There are numerous methods of transcriptomic analysis known in the art, and all of the known methods are deemed suitable for use herein. For example, preferred materials include mRNA and primary transcripts (hnRNA), and RNA sequence information may be obtained from reverse transcribed polyA$^+$-RNA, which is in turn obtained from a tumor sample and a matched normal (healthy) sample of the same patient. Likewise, it should be noted that while polyA+-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis, especially including RNAseq. In other aspects, RNA quantification and sequencing is performed using qPCR and/or rtPCR based methods, although various alternative methods (e.g., solid phase hybridization-based methods) are also deemed suitable. Viewed from another perspective, transcriptomic analysis may be suitable (alone or in combination with genomic analysis) to identify and quantify genes having a cancer- and patient-specific mutation.

Similarly, proteomics analysis can be performed in numerous manners to ascertain actual translation of the RNA of the neoepitope, and all known manners of proteomics analysis are contemplated herein. However, particularly preferred proteomics methods include antibody-based methods and mass spectroscopic methods. Moreover, it should be noted that the proteomics analysis may not only provide qualitative or quantitative information about the protein per se, but may also include protein activity data where the protein has catalytic or other functional activity. One exemplary technique for conducting proteomic assays is described in U.S. Pat. No. 7,473,532, incorporated by reference herein. Further suitable methods of identification and even quantification of protein expression include various mass spectroscopic analyses (e.g., selective reaction monitoring (SRM), multiple reaction monitoring (MRM), and consecutive reaction monitoring (CRM)).

In yet another aspect of filtering, the neoepitopes may be compared against a database that contains known human sequences (e.g., of the patient or a collection of patients) to so avoid use of a human-identical sequence. Moreover, filtering may also include removal of neoepitope sequences that are due to SNPs in the patient where the SNPs are present in both the tumor and the matched normal sequence. For example, dbSNP (The Single Nucleotide Polymorphism Database) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation. Using such database and other filtering options as described above, the patient and tumor specific neoepitopes may be filtered to remove those known sequences, yielding a sequence set with a plurality of neoepitope sequences having substantially reduced false positives.

In less preferred aspects, cancer- and patient-specific neoepitopes may be augmented with or even replaced by more common neoepitopes. For example, contemplated common neoepitopes include various cancer associated and cancer specific antigens (e.g., having a frequency of at least 0.1%, or at least 0.5%, or at least 1%, or at least 5%). Alternatively, suitable neoantigens may also include those identified as occurring in at least one specific MHC sub-type at a predetermined minimum frequency (e.g., having a frequency of at least 0.1%, or at least 0.5%, or at least 1%, or at least 5%). Further aspects of neoepitopes, methods, and systems related to same are disclosed in our commonly owned International applications PCT/US16/26798 and PCT/US16/29244, both incorporated by reference herein.

HLA Determination and Matching

The human major histocompatibility complex (MHC), or human leukocyte antigen (HLA) complex, comprises many genetic loci, including at least seven loci that encode two distinct classes of highly polymorphic cell surface antigens that are co-expressed. These molecules bind and present processed peptides to circulating T-cell lymphocytes and are crucial to both cellular and humoral immune responses. Consequently, in the context of immune therapeutics it should be readily apparent that neoepitopes will be more likely effective where the neoepitopes are bound to and presented by the MHC complexes.

Figure 1A:
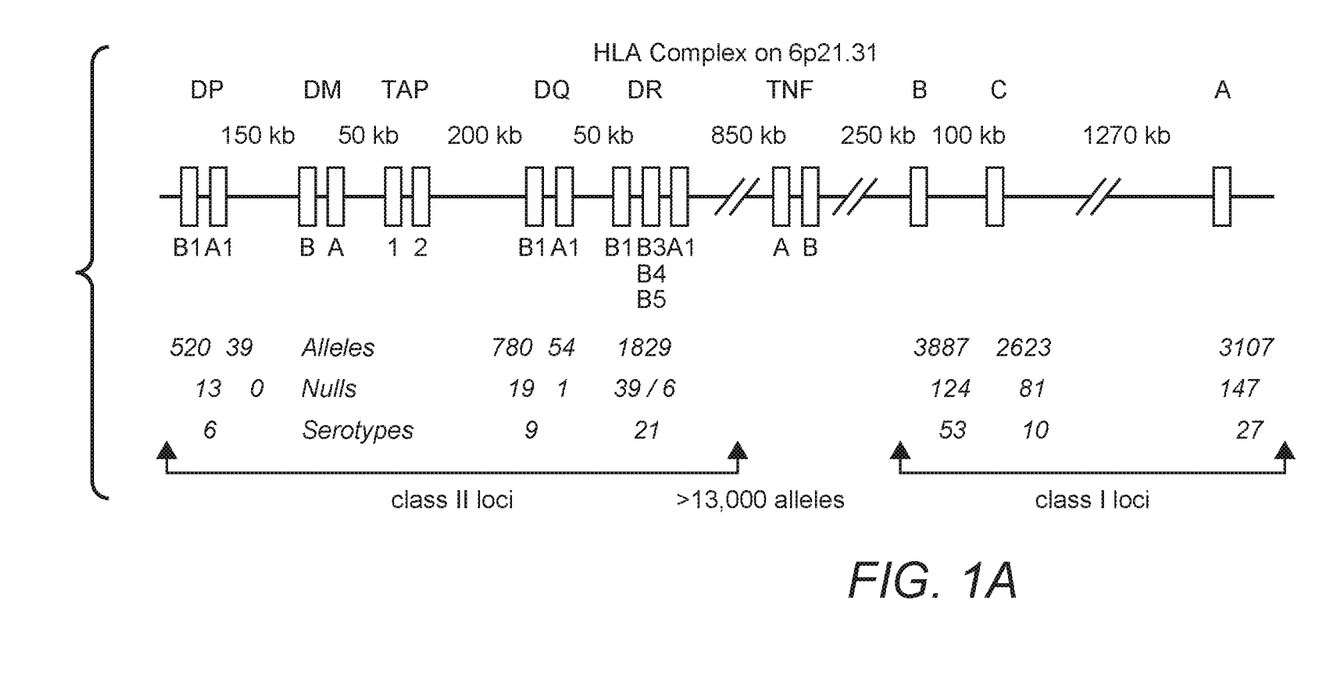
FIGS. 1A and 1B are exemplary schematic illustrations of locations of HLA-types on a human chromosome, allele diversity (FIG. 1A) and expression and membrane location (FIG. 1B).
Figure 1B:
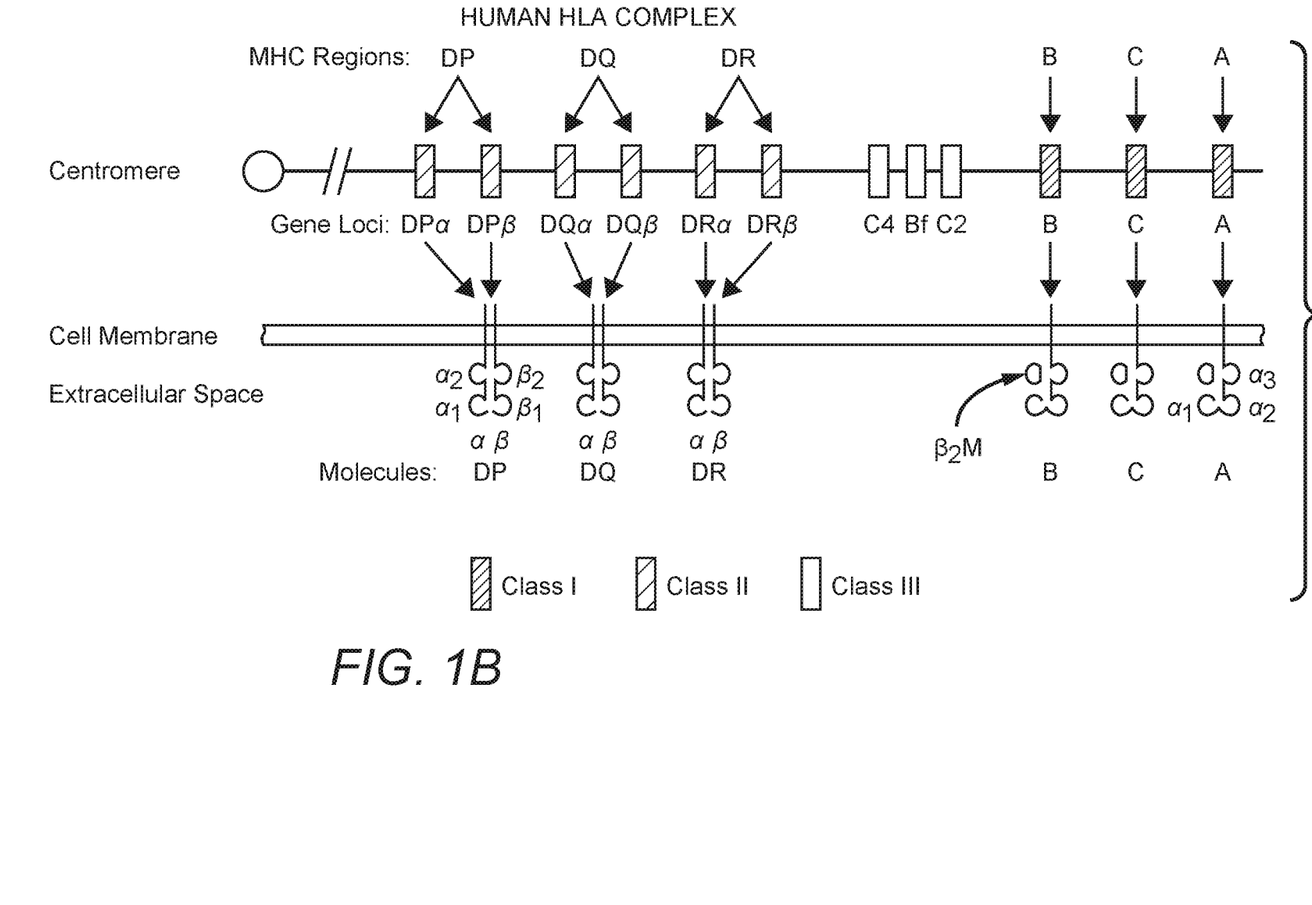

Unfortunately, however, the MHC complexes are highly diverse and distinct among different patients, rendering neoepitope binding predictions difficult. The class I molecules, HLA-A, HLA-B and HLA-C, and the class II molecules, DR, DQ and DP, are encoded in a approximately 3500 kbp segment of the short arm of chromosome 6p21.31 (schematically illustrated FIGS. 1A and 1B). Class I antigens are presented on all nucleated cells, where they act as cell surface heterodimers that primarily present peptides derived from the cytosol (viral and self peptides) to circulating CD8+ T cells. The class I cell surface heterodimer has one highly polymorphic alpha chain, with variable residues clustering within the peptide binding cleft, which is encoded by exons 2 and 3 of the gene. The HLA class I molecules also act as ligands for killer immunoglobulin receptors (KIR), which regulate the cytotoxic activity of natural killer (NK) cells. HLA class II molecules are found on the surface of B cells, macrophages and other antigen presenting cells, where the alpha-beta heterodimer presents primarily exogenously derived peptides (bacteria and chemical toxins) to circulating CD4+ T cells. In class II molecules, the beta chain contains the highly polymorphic regions, which are localized to exon 2 of the gene and encode the peptide-binding cleft.

Consequently, it should be appreciated that effective binding and presentation is a combined function of the sequence of the neoepitope and the particular HLA-type of a patient. Most typically, the HLA-type determination includes at least three MHC-I sub-types (e.g., HLA-A, HLA-B, HLA-C) and at least three MHC-II sub-types (e.g., HLA-DP, HLA-DQ, HLA-DR), preferably with each subtype being determined to at least 4-digit depth. However, greater depth (e.g., 6 digit, 8 digit) is also contemplated herein.

One the HLA-type of the patient is ascertained (using known chemistry or in silico determination), a structural solution for the HLA-type is calculated or obtained from a database, which is then used in a docking model in silico to determine binding affinity of the (typically filtered) neoepitope to the HLA structural solution. As will be further discussed below, suitable systems for determination of binding affinities include the NetMHC platform (see e.g., Nucleic Acids Res. 2008 Jul. 1; 36 (Web Server issue): W509-W512.). Neoepitopes with high affinity (e.g., less than 100 nM, less than 75 nM, less than 50 nM) for a previously determined HLA-type are then selected for therapy creation, along with the knowledge of the MHC-I/II subtype.

HLA determination can be performed using various methods in wet-chemistry that are well known in the art, and all of these methods are deemed suitable for use herein. However, in especially preferred methods, the HLA-type can also be predicted from omics data in silico using a reference sequence containing most or all of the known and/or common HLA-types as is shown in more detail below.

For example, in one preferred method according to the inventive subject matter, a relatively large number of patient sequence reads mapping to chromosome 6p21.3 (or any other location near/at which HLA alleles are found) is provided by a database or sequencing machine. Most typically the sequence reads will have a length of about 100-300 bases and comprise metadata, including read quality, alignment information, orientation, location, etc. For example, suitable formats include SAM, BAM, FASTA, GAR, etc. While not limiting to the inventive subject matter, it is generally preferred that the patient sequence reads provide a depth of coverage of at least 5×, more typically at least 10×, even more typically at least 20×, and most typically at least 30×.

In addition to the patient sequence reads, contemplated methods further employ one or more reference sequences that include a plurality of sequences of known and distinct HLA alleles. For example, a typical reference sequence may be a synthetic (without corresponding human or other mammalian counterpart) sequence that includes sequence segments of at least one HLA-type with multiple HLA-alleles of that HLA-type. For example, suitable reference sequences include a collection of known genomic sequences for at least 50 different alleles of HLA-A. Alternatively, or additionally, the reference sequence may also include a collection of known RNA sequences for at least 50 different alleles of HLA-A. Of course, and as further discussed in more detail below, the reference sequence is not limited to 50 alleles of HLA-A, but may have alternative composition with respect to HLA-type and number/composition of alleles. Most typically, the reference sequence will be in a computer readable format and will be provided from a database or other data storage device. For example, suitable reference sequence formats include FASTA, FASTQ, EMBL, GCG, or GenBank format, and may be directly obtained or built from data of a public data repository (e.g., IMGT, the International ImMunoGeneTics information system, or The Allele Frequency Net Database, EUROSTAM, www.allelefrequencies.net). Alternatively, the reference sequence may also be built from individual known HLA-alleles based on one or more predetermined criteria such as allele frequency, ethnic allele distribution, common or rare allele types, etc.

Using the reference sequence, the patient sequence reads can now be threaded through a de Bruijn graph to identify the alleles with the best fit. In this context, it should be noted that each individual carries two alleles for each HLA-type, and that these alleles may be very similar, or in some cases even identical. Such high degree of similarity poses a significant problem for traditional alignment schemes. The inventor has now discovered that the HLA alleles, and even very closely related alleles can be resolved using an approach in which the de Bruijn graph is constructed by decomposing a sequence read into relatively small k-mers (typically having a length of between 10-20 bases), and by implementing a weighted vote process in which each patient sequence read provides a vote ("quantitative read support") for each of the alleles on the basis of k-mers of that sequence read that match the sequence of the allele. The cumulatively highest vote for an allele then indicates the most likely predicted HLA allele. In addition, it is generally preferred that each fragment that is a match to the allele is also used to calculate the overall coverage and depth of coverage for that allele.

Scoring may further be improved or refined as needed, especially where many of the top hits are similar (e.g., where a significant portion of their score comes from a highly shared set of k-mers). For example, score refinement may include a weighting scheme in which alleles that are substantially similar (e.g., >99%, or other predetermined value) to the current top hit are removed from future consideration. Counts for k-mers used by the current top hit are then re-weighted by a factor (e.g., 0.5), and the scores for each HLA allele are recalculated by summing these weighted counts. This selection process is repeated to find a new top hit. The accuracy of the method can be even further improved using RNA sequence data that allows identification of the alleles expressed by a tumor, which may sometimes be just 1 of the 2 alleles present in the DNA. In further advantageous aspects of contemplated systems and methods, DNA or RNA, or a combination of both DNA and RNA can be processed to make HLA predictions that are highly accurate and can be derived from tumor or blood DNA or RNA. Further aspects, suitable methods and considerations for high-accuracy in silico HLA typing are described in International PCT/US16/48768, incorporated by reference herein.

Where desired, neoepitopes can be scored/ranked based on allele frequency multiplied by the transcripts per million number to get a likelihood score. This score can then be further augmented using HLA information and calculated for actual binding affinity to the patient's HLA type. For example, an exemplary ranking format may be:
>254 NM_001000.3 RPL39 Missense p.M29K A→T Normal: WIRMKTGNK, AF: 0.179104477612 TPM: 1023.96 TPM_MEDIAN: 7.35 LL: 183.395820896 netMHC: 242.96 Allele: HLA-A0301 WIRKKTGNK.

Here, the file is a FASTA formatted file, and entries start with the '>' character, which just reports sample information. The next line is the neoepitope. In the sample information line contains a number used for indexing the sample (e.g., 254), the Refseq Gene ID (e.g., NM_001000.3), the HUGO common name (e.g., RPL39), the variant classification (e.g., Missense), the protein change (e.g., p.M29K), the base pair change (e.g., A→T), the normal epitope (e.g., Normal: WIRMKTGNK), allele frequency (e.g., AF: 0.179104477612), Transcripts per million for this gene (e.g., TPM: 1023.96), TPM_MEDIAN which is the median expression level of all the genes (e.g., TPM_MEDIAN: 7.35), the LL score which is just AF×TPM (e.g., LL: 183.395820896), the netMHC predicted binding value (e.g., netMHC: 242.96), and the specific HLA allele that the neoepitope binds to (e.g., Allele: HLA-A0301). The next line is then the neoepitope (e.g., WIRKKTGNK).

Once patient and tumor specific neoepitopes and HLA-type are identified, further computational analysis can be performed by docking neoepitopes to the HLA and determining best binders (e.g., lowest $K_D$, for example, less than 500 nM, or less than 250 nM, or less than 150 nM, or less than 50 nM), for example, using NetMHC. It should be appreciated that such approach will not only identify specific neoepitopes that are genuine to the patient and tumor, but also those neoepitopes that are most likely to be presented on a cell and as such most likely to elicit an immune response with therapeutic effect. Of course, it should also be appreciated that thusly identified HLA-matched neoepitopes can be biochemically validated in vitro prior to inclusion of the nucleic acid encoding the epitope as payload into the virus as is further discussed below.

Of course, it should be appreciated that matching of the patient's HLA-type to the patient- and cancer-specific neoepitope can be done using systems other than NetMHC, and suitable systems include NetMHC II, NetMHCpan, IEDB Analysis Resource (URL immuneepitope.org), Rank-Pep, PREDEP, SVMHC, Epipredict, HLABinding, and others (see e.g., *J Immunol Methods* 2011; 374:1-4). In calculating the highest affinity, it should be noted that the collection of neoepitope sequences in which the position of the altered amino acid is moved (supra) can be used. Alternatively, or additionally, modifications to the neoepitopes may be implemented by adding N- and/or C-terminal modifications to further increase binding of the expressed neoepitope to the patient's HLA-type. Thus, neoepitopes may be native as identified or further modified to better match a particular HLA-type.

Moreover, where desired, binding of corresponding wild type sequences (i.e., neoepitope sequence without amino acid change) can be calculated to ensure high differential affinities. For example, especially preferred high differential affinities in MHC binding between the neoepitope and its corresponding wild type sequence are at least 2-fold, at least 5-fold, at least 10-fold, at least 100-fold, at least 500-fold, at least 1000-fold, etc.).

Figure 2:
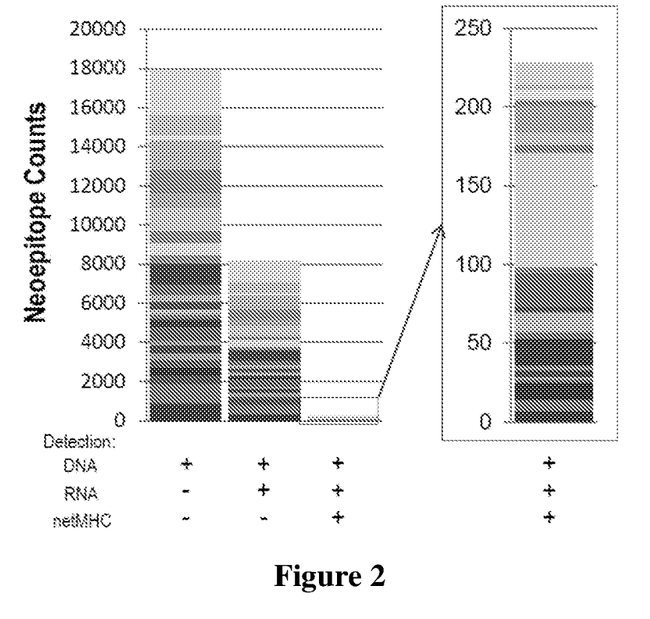
FIG. 2 is an exemplary plot depicting filtering outcomes for calculated neoepitopes.

FIG. 2 exemplarily shows a typical outcome of a series of filtering steps. Here, whole genome sequencing analysis of a triple negative breast cancer sample against matched normal (i.e., compared against non-diseased tissue of the same patient) in a synchronous location guided alignment revealed a relatively large number (~18,000) of neoepitopes in the tumor sample. Notably, a first filtering step removed more than 50% of all of the identified neoepitopes on the basis of expression strength. Here, neoepitope sequences were removed with an expression level of less than 20% of expression as compared to the matched normal sample. The remaining sequences were subjected to an in silico analysis to determine those sequences that would bind (e.g., less than 500 nM affinity) to a single specific HLA-type of the same sample. It should be noted that once more a substantial fraction of neoepitopes was eliminated, and that ultimately only less than 1.3% of all neoepitopes were found suitable for use.

It should be noted that such analysis is particularly advantageous for HLA determination from DNA and/or RNA sequencing information since each HLA-type has numerous often very similar alleles, and as traditional alignment methods typically fail to have significant differentiation capabilities where sequences have high degree of similarity. Moreover, it should be appreciated that such analysis is advantageously performed from sequencing omics data already obtained from the patient without the need for dedicated laboratory equipment. Viewed from a different perspective, neoepitope discovery, filtering, HLA-type determination, and even binding of the so identified neoepitopes to the particular HLA type of the patient can all be done in silico.

Choice of Co-Stimulatory Molecules

With respect to suitable co-stimulatory molecules it is generally contemplated that all co-stimulatory molecules are deemed appropriate so long as such molecules have an up-regulating effect with regard to T-cell activation when expressed in an antigen presenting cell. For example, FIG. 3 exemplarily illustrates co-stimulatory molecules on a dendritic cell and their receptors on a T-cell.

Figure 3:
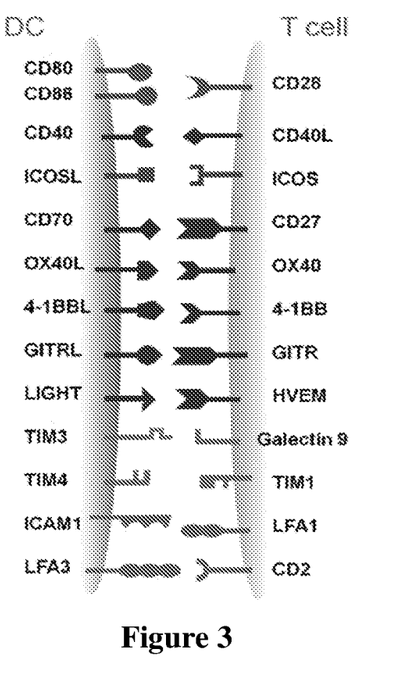
FIG. 3 is an graphical representation of exemplary interactions of co-stimulatory receptors and ligands during activation of T-cells.

Contemplated up-regulating effects may be due to the suppression of co-inhibition (e.g., mediated by CTLA4, PD1, CD160, or BTLA), and/or due to the activation of co-stimulatory receptors at the T-cell (e.g., via CD28, CD40L, ICOS, CD27, OX40, 4-1BB, GITR, HVEM, Galectin9, TIM1, LFA, CD2, etc). Therefore, suitable co-stimulatory molecules include B7.1 (CD80), B7.2 (CD86), CD40, ICOSL CD70, OX40L, 4-1BB, GITRL, LIGHT, TIM3, TIM4, ICAM1, and LFA3. Alternatively or additionally, contemplated co-stimulatory molecules may also be selected by their particular function in activation. For example, co-stimulatory molecules may be selected due to their role in the formation and/or maintenance of the immune synapse, and/or due to their role in downstream activation events. Therefore, suitable co-stimulatory molecules include one or more components of the supramolecular activation cluster (SMAC), including elements of cSMAC (e.g. CD2, CD4, CD8, CD28, Lck, and/or Fyn, or their binding counterparts), pSMAC (e.g., LFA1 or its binding counterpart), and d-SMAC (e.g., CD43, CD45 or their binding counterparts). For example, where more than one co-stimulator molecule is employed, at least two of ICAM-1, CD60, CD80, CD86, and/or CD 48 may be particularly desirable.

Most typically, contemplated recombinant nucleic acids for transfection of cells (and especially antigen presenting cells such as dendritic cells) will preferably include in addition to one or more neoepitope sequences also more than one sequence element that encodes a co-stimulatory molecule as discussed above. Indeed, it is generally contemplated that suitable recombinant nucleic acids will include at least two, or at least three, or at least four sequence elements that encode co-stimulatory molecules. Most typically, where multiple co-stimulatory molecules are present, it is contemplated that the co-stimulatory molecules provide a synergistic effect with respect to T-cell activation/activity. Consequently, it should be appreciated that the recombinant nucleic acid will be configured such that the co-stimulatory molecules and the neoepitopes will be contemporaneously expressed (which may, for example, be achieved using a single promoter or multiple inducible promoters). In addition, it should also be appreciated that the co-stimulatory molecules may be expressed together with the suitable ligand or receptor, either on a single polypeptide chain or as two distinct molecules. For example, where the expressed receptor is OX40, the receptor may be co-expressed with OX40L. Likewise, where the expressed ligand is 4-1BBL, the ligand may be co-expressed with 4-1BB. In addition, while it is generally preferred that the co-stimulatory molecules are expressed with their respective membrane domains to so allow for membrane anchoring in the cell expressing the co-stimulatory molecules, it should be noted that the nucleic acid encoding the co-stimulatory molecules may be modified such that the ligand (and in some cases the receptor) may be expressed in a soluble form.

Additionally, it should be appreciated that the recombinant nucleic acid may also encode one or more cytokines, and especially preferred cytokines include IL-2, IL-7, IL-12, IL-15, an IL-15 superagonist (e.g., IL15N72D), and an IL-15 superagonist/IL-15RαSushi-Fc fusion complex (e.g., ALT803). Such cytokine is typically co-expressed with the neoepitopes and co-stimulatory molecules to further enhance immune activation. In further contemplated aspects, co-stimulatory molecules will also include various additional immune stimulatory components, and contemplated additional components include various SLAM (signaling lymphocyte activation molecules) proteins such as CD84, CD150, CD229, and/or CD244, which are preferably co-expressed with the selected neoepitopes and/or co-stimulatory molecules.

Likewise, in further contemplated aspects, the additional components may also be positive regulators of innate immune response pathways, and especially of the STING (Stimulator of Interferon Gene) pathway. Among other suitable positive regulators, especially preferred positive regulators include chimeric proteins in which the transmembrane domain of LMP1 of EBV is fused to the signaling domain of a signaling protein associated with the STING pathway, and particularly with the signaling domain of IPS1 as is described, for example, in WO 2014/039961. SEQ ID NO:1 provides an exemplary chimeric molecule in which the transmembrane domain of LMP1 of EBV is fused to the signaling domain of murine IPS1.

In such chimeric proteins, it is generally preferred to have at least one, more typically at least two, more typically at least 3, and most typically at least six transmembrane domain of the LMP1 protein fused to at least one, or at least two, or at least three IPS signaling domains. Of course, it should be noted that while the signaling domains of IPS1 are preferred, other activators also deemed suitable for use herein and particularly include various protein receptors in the Tumor Necrosis Factor Receptor Super Family (TNFRSF).

Latent membrane protein-1 (LMP1) is a gene in the Epstein-Barr Virus (EBV). The N-terminus comprises six contiguous transmembrane domains that anchor the protein into the membrane. The intracytoplasmic domain of LMP1 is analogous to the signaling domain of the CD40 receptor, a TNFRSF, and can be replaced by one or more IPS1 signaling domains. Notably, LMP1 needs no ligand or antibody to initiate signaling through its cytoplasmic domain since its N-terminal transmembrane domain spontaneously forms clusters in the cell membrane and thereby clusters the intracytoplasmic signaling domains. By replacement of the intracytoplasmic domain of LMP1 with IPS1 signaling domains, constitutive activation of the STING pathway is achieved. Of course, it should be recognized that such chimeric proteins may be co-expressed with the other co-stimulatory molecules and/or neoepitopes to so provide an enhanced immune stimulation. In such case, it is contemplated that the combination of co-stimulatory molecules and chimeric immune activators may act synergistically due to activation of T-cells via two distinct pathways: STING related gene expression and activating immune synapse formation.

Virus Construction

Upon selection of preferred patient- and cancer-specific HLA matched neoepitopes, and suitable co-stimulatory molecules/chimeric activators, a recombinant nucleic acid can be constructed for intracellular expression and subsequent presentation of the neoepitopes on the cell. The recombinant nucleic acid comprises sequence portions that encode one or more patient- and cancer-specific neoepitopes in an arrangement such that the neoepitope is directed to MHC-I and/or MHC-II presentation pathways and MHC sub-type(s) for which the neoepitope is known to have high affinity. In addition, the recombinant nucleic acid will also include sequence portions encoding the appropriate co-stimulatory molecules/chimeric activators. MHC-targeted and rational-based presentation is thought to produce a more robust immune response, which will be further augmented by co-expression of one or more co-stimulatory molecules and/or chimeric activators.

Of course, it should be appreciated that all manners of delivery of such recombinant nucleic acid(s) are deemed suitable and that the recombinant nucleic acid(s) may be formulated as a DNA vaccine, as a recombinant viral genome, or a DNA or RNA deliverable in a transfection composition. Therefore, it is noted that all expression systems known in the art are deemed suitable for use herein (e.g., bacterial expression systems, yeast expression systems, 'naked' DNA and RNA expression systems).

Similarly, and depending on the particular recombinant nucleic acid formulation, the type of transfected cell may vary considerably. However, it is generally preferred that the cells are immune competent cells, and especially antigen presenting cells (dendritic cells, macrophages, etc.). Such cells will preferably be autologous to the patient or individual receiving the recombinant cell, and autologous cells may be enriched or cultured cells. For example, dendritic cells may be isolated by initial B-cell and monocyte depletion of whole blood (e.g., via CD14/19 markers), followed by magnetic separation of dendritic cells using appropriate dendritic cell markers (e.g., CD304, CD141, and CD1c). Alternatively, dendritic cells may also be cultivated from stem cells (see e.g., *World J Stem Cells* 2014 Jan. 26; 6(1): 1-10). In still further contemplated aspects, and especially where the recombinant nucleic acid is a viral expression vector, the patient may be infected with the virus (e.g., using subcutaneous or intratumoral injection), especially where the virus is an adenovirus.

For example, it is especially preferred to use viruses already established in gene therapy, including adenoviruses, adeno-associated viruses, alphaviruses, herpes viruses, lentiviruses, etc. However, among other appropriate choices, adenoviruses are particularly preferred. Moreover, it is further generally preferred that the virus is a replication deficient and non-immunogenic virus, which is typically accomplished by targeted deletion of selected viral proteins (e.g., E1, E3 proteins). The term "non-immunogenic" as used herein means that the virus can be repeatedly administered to an individual without causing an immune reaction that eradicates the virus. Such desirable properties may be further enhanced by deleting E2b gene function, and high titers of recombinant viruses can be achieved using genetically modified human 293 cells as has been recently reported (e.g., *J Virol* 1998 February; 72(2): 926-933). Most typically, the desired nucleic acid sequences (for expression from virus infected cells) are under the control of appropriate regulatory elements well known in the art.

With respect to the integration of sequence portions that encode the neoepitopes and co-stimulatory molecules and/or chimeric activators it should be noted that the various sequence elements may be arranged in numerous manners. For example, a transcription or translation unit may have concatemeric arrangement of multiple epitopes, typically separated by short linkers (e.g., flexible linkers having between 4 and 20 amino acids), which may further include protease cleavage sites. Such concatemers may include between 1 and 20 neoepitopes (typically limited by size of recombinant nucleic acid that can be delivered via a virus), and it should be noted that the concatemers may be identical for delivery to the MHC-I and MHC-II complex, or different. Therefore, and as noted below, it should be appreciated that various peptides can be routed to specific cellular compartments to so achieve preferential or even specific presentation via MHC-I and/or MHC-II. Viewed from another perspective, it should be recognized that tumor associated antigens and neoepitopes may be presented via both presentation pathways, or selectively to one or another pathway at the same time or in subsequent rounds of treatment. The co-stimulatory molecules and/or chimeric activators will preferably expressed as isolated peptide units as further discussed below. Moreover, the recombinant nucleic acid encoding the co-stimulatory molecules and/or chimeric activators will typically also include sequence elements that direct the recombinant proteins to the cell membrane for anchoring the proteins onto the membrane.

With respect to the 'payload' of the genetically modified virus it is contemplated that expression of more than one neoepitope is preferred, for example two, three, four, five, and even more, which can be accomplished using multiple distinct modified viruses, or a virus having more than one neoepitope sequence (e.g., as concatemeric or chimeric sequence). While not limiting to the inventive subject matter, it is generally preferred that neoepitope sequences are configured as a tandem minigene (e.g., $aa_{12}$-neoepitope$_{12}$-$aa_{12}$), or as single transcriptional unit, which may or may not be translated to a chimeric protein. Thus, it should be appreciated that the epitopes can be presented as monomers, multimers, individually or concatemeric, or as hybrid sequences with N- and/or C-terminal peptides. Most typically, it is preferred that the nucleic acid sequence is back-translated using suitable codon usage to accommodate the virus and/or host codon preference. However, alternate codon usage or non-matched codon usage is also deemed appropriate. With respect to further suitable configurations and expression cassettes reference is made to co-pending US provisional applications with the Ser. No. 62/302,168, filed Mar. 2, 2016, and the Ser. No. 62/314,366, filed Mar. 28, 2016, incorporated by reference herein.

It should be further appreciated that neoepitope sequences (e.g., expressed as single neoepitope or as polytope) may be configured and directed to one or both MHC presentation pathways using suitable sequence elements. With respect to routing the so expressed neoepitopes to the desired MHC-system, it is noted that the MHC-I presented peptides will typically arise from the cytoplasm via proteasome processing and delivery through the endoplasmatic reticulum. Thus, expression of the epitopes intended for MHC-I presentation will generally be directed to the cytoplasm as is further discussed in more detail below. On the other hand, MHC-II presented peptides will typically arise from the endosomal and lysosomal compartment via degradation and processing by acidic proteases (e.g., legumain, cathepsin L and cathepsin S) prior to delivery to the cell membrane. Thus, expression of the epitopes intended for MHC-II presentation will generally be directed to the endosomal and lysosomal compartment as is also discussed in more detail below.

In most preferred aspects, signal peptides may be used for trafficking the neoepitopes to the endosomal and lysosomal compartment (and with directing the neoepitope presentation towards MHC-II), or for retention in the cytoplasmic space (and with directing the neoepitope presentation towards MHC-I). For example, where the peptide is to be exported to the endosomal and lysosomal compartment targeting presequences and the internal targeting peptides can be employed. The presequences of the targeting peptide are preferably added to the N-terminus and comprise between 6-136 basic and hydrophobic amino acids. In case of peroxisomal targeting, the targeting sequence may be at the C-terminus. Other signals (e.g., signal patches) may be used and include sequence elements that are separate in the peptide sequence and become functional upon proper peptide folding. In addition, protein modifications like glycosylations can induce targeting. Among other suitable targeting signals, the inventors contemplate peroxisome targeting signal 1 (PTS1), a C-terminal tripeptide, and peroxisome targeting signal 2 (PTS2), which is a nonapeptide located near the N-terminus. In addition, sorting of proteins to endosomes and lysosomes may also be mediated by signals within the cytosolic domains of the proteins, typically comprising short, linear sequences. Some signals are referred to as tyrosine-based sorting signals and conform to the NPXY or YXXØ consensus motifs. Other signals known as dileucine-based signals fit [DE]XXXL[LI] or DXXLL consensus motifs. All of these signals are recognized by components of protein coats peripherally associated with the cytosolic face of membranes. YXXØ and [DE]XXXL[LI] signals are recognized with characteristic fine specificity by the adaptor protein (AP) complexes AP-1, AP-2, AP-3, and AP-4, whereas DXXLL signals are recognized by another family of adaptors known as GGAs. Also FYVE domain can be added, which has been associated with vacuolar protein sorting and endosome function. In still further aspects, endosomal compartments can also be targeted using human CD1 tail sequences (see e.g., *Immunology*, 122, 522-531).

Trafficking to or retention in the cytosolic compartment may not necessarily require one or more specific sequence elements. However, in at least some aspects, N- or C-terminal cytoplasmic retention signals may be added, including a membrane-anchored protein or a membrane anchor domain of a membrane-anchored protein. For example, membrane-anchored proteins include SNAP-25, syntaxin, synaptoprevin, synaptotagmin, vesicle associated membrane proteins (VAMPs), synaptic vesicle glycoproteins (SV2), high affinity choline transporters, Neurexins, voltage-gated calcium channels, acetylcholinesterase, and NOTCH.

Additionally, it is contemplated that the viral delivery vehicle also encodes at least one, more typically at least two, even more typically at least three, and most typically at least four co-stimulatory molecules to enhance the interaction between the infected dendritic cells and T-cells. For example, suitable co-stimulatory molecules include ICAM-1 (CD54), ICOS-L, and LFA-3 (CD58), especially in combination with B7.1 (CD80) and/or B7.2 (CD86). Further contemplated co-stimulatory molecules include 4-1BBL, CD30L, CD40, CD40L, CD48, CD70, CD112, CD155, GITRL, OX40L, and TL1A. Moreover, it should be appreciated that expression of the co-stimulatory molecules will preferably be coordinated such that the antigens and/or neoepitopes are presented along with one or more co-stimulatory molecules. Thus, it is typically contemplated that the co-stimulatory molecules are produced from a single transcript, for example, using an internal ribosome entry site or 2A sequence, or from multiple transcripts.

Likewise, it is contemplated that the viral vector will further include a sequence portion that encodes one or more peptide ligands that bind to a checkpoint receptor. Most typically, binding will inhibit or at least reduce signaling via the receptor, and particularly contemplated receptors include CTLA-4 (especially for CD8+ cells) PD-1 (especially for CD4+ cells). For example, peptide binders can include antibody fragments and especially scFv, but also small molecule peptide ligands that specifically bind to the receptors. Once more, it should be appreciated that expression of the peptide molecules will preferably be coordinated such that the antigens and/or neoepitopes are presented along with one or more peptide molecules. Thus, it is typically contemplated that the peptide molecules are produced from a single transcript, for example, using an internal ribosome entry site or 2A sequence, or from multiple transcripts.

Viruses may then be individually or in combination used as a therapeutic vaccine in a pharmaceutical composition, typically formulated as a sterile injectable composition with a virus titer of between $10^4$-$10^{11}$ virus particles per dosage unit. Alternatively, the virus may be employed to infect patient (or other HLA matched) cells ex vivo and the so infected cells are then transfused to the patient. In further examples, treatment of patients with the virus may be accompanied by allografted or autologous natural killer cells or T cells in a bare form or bearing chimeric antigen receptors expressing antibodies targeting neoepitope, neoepitopes, tumor associated antigens or the same payload as the virus. The natural killer cells, which include the patient-derived NK-92 cell line, may also express CD16 and can be coupled with an antibody. As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Where desired, it is also contemplated that administration of the recombinant virus may be performed together with administration of immune check point inhibitors. For example, suitable check point inhibitors include agents targeting PD-1 (e.g., nivolumab, pembrolizumab), CTLA-4 (e.g., ipilimumab), or other receptors that, upon ligand binding, downregulate T-cell activity.

Lastly, it should be noted that where the virus comprises a nucleic acid payload that encodes multiple neoepitopes, it is contemplated that multiple neoepitopes may at least additively or synergistically enhance the host immune response. Similarly, where multiple viruses are used with each virus having a different neoepitope, it is contemplated that multiple neoepitopes may at least additively or synergistically enhance the host immune response. Such additive or synergistic effect may be genuine to a specific tumor or stage, or specific to particular patient parameter (e.g., age, gender, previous treatment, etc.).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of generating a recombinant virus, comprising:
assaying deoxyribonucleic acid (DNA), ribonucleic acid (RNA), and protein from matched tumor and histologically normal tissue samples from a patient to identify a patient-specific cancer-related neoepitope of the patient, wherein the protein assay is mass spectroscopy based sequencing;
determining binding of the patient-specific cancer-related neoepitope to an HLA-type of the same patient, and determining an expression level of the patient-specific cancer-related neoepitope;
selecting at least one co-stimulatory molecule; and
genetically modifying a virus to include a nucleic acid encoding the at least one co-stimulatory molecule and the patient-specific cancer-related neoepitope.

2. The method of claim 1 wherein the cancer-related neoepitope of the patient is identified in silico by location-guided synchronous alignment of omics data of tumor and matched normal samples.

3. The method of claim 1 further comprising a step of predicting the HLA type of the patient in silico.

4. The method of claim 1 wherein the expression level is at least 20% compared to a matched normal sample.

5. The method of claim 1 wherein the co-stimulatory molecule is selected from the group of B7.1 (CD80), B7.2 (CD86), CD30L, CD40, CD40L, CD48, CD70, CD112, CD155, ICOS-L Inducible T-cell costimulatory ligand or CD278, 4-1BB CD137, GITR-L (Glucocorticoid-Induced TNFR-Related protein), LIGHT (tumor necrosis factor superfamily member 14 or TNFSF14, TIM3, TIM4, ICAM-1 (Intercellular Adhesion Molecule 1 CD54), and LFA3 (CD58).

6. The method of claim 1 wherein the nucleic acid further comprises a sequence encoding a cytokine, wherein the cytokine is selected from the group consisting of IL-2, IL-7, IL-12, IL-15, an IL-15 superagonist (IL-15N72D), and an IL-15 superagonist/IL-15RαSushi-Fc fusion complex.

7. The method of claim 1 wherein the nucleic acid further comprises a sequence encoding at least one component of a SMAC (supramolecular activation cluster) wherein the at least one component of the SMAC is selected form the group consisting of CD2, CD4, CD8, CD28, Lck, Fyn, LFA-1, CD43, and CD45 or their respective binding counterparts.

8. The method of claim 1 wherein the nucleic acid further comprises a sequence encoding an activator of a STING (Stimulator of Interferon Gene) pathway, wherein the activator of the STING pathway comprises a chimeric protein in which a transmembrane domain of LMP1 (Latent membrane protein 1) of EBV is fused to a signaling domain of IPS-1 (IFN-β promter stimulator 1.).

9. The method of claim 1 further comprising a step of including into the nucleic acid a segment that encodes at least a second distinct disease-related neoepitope.

10. A method of treating a patient, comprising:
obtaining a tumor sample and a matched histologically normal sample from the patient;
assaying deoxyribonucleic acid (DNA), ribonucleic acid (RNA), and protein from matched tumor and histologically normal tissue samples to identify an HLA-type of the patient and identify a patient-specific cancer-related neoepitope of the same patient, wherein the protein assay is mass spectroscopy based sequencing;
genetically modifying a virus to include (i) a nucleic acid encoding the neoepitope when the binding affinity is below a predetermined threshold value, and (ii) a nucleic acid encoding at least one co-stimulatory molecule; and
administering the genetically modified virus to the patient.

11. The method of claim 10 wherein the steps of identifying the HLA-type and identifying the cancer-related neoepitope of the patient is performed in silico using genomic information from the tumor sample and the matched normal sample.

12. The method of claim 10 wherein the co-stimulatory molecule is selected from the group of B7.1 (CD80), B7.2 (CD86), CD30L, CD40, CD40L, CD48, CD70, CD112, CD155, ICOS-L, 4-1BB, GITR-L, LIGHT, TIM3, TIM4, ICAM-1, and LFA3 (CD58).

13. The method of claim 10 wherein the virus further comprises a nucleic acid encoding a cytokine, wherein cytokine is selected from the group consisting of IL-2, IL-7, IL-12, IL-15, an IL-15 superagonist (IL-15N72D), and an IL-15 superagonist/IL-15RαSushi-Fc fusion complex.

14. The method of claim 10 wherein the virus further comprises a nucleic acid encoding at least one component of a SMAC (supramolecular activation cluster), wherein the at least one component of the SMAC is selected form the group consisting of CD2, CD4, CD8, CD28, Lck, Fyn, LFA-1, CD43, and CD45 or their respective binding counterparts.

15. The method of claim 10 wherein the virus further comprises a nucleic acid encoding an activator of a STING (Stimulator of Interferon Gene) pathway, wherein the activator of the STING pathway comprises a chimeric protein in which a transmembrane domain of LMP1 of EBV is fused to a signaling domain of IPS-1.

16. The method of claim 10 wherein the virus is an adenovirus.

17. The method of claim 16 wherein the adenovirus is an Ad5 [E1⁻E2b⁻].

18. The method of claim 10 wherein the virus further comprises a nucleic acid encoding at least one additional cancer-related neoepitope.

19. The method of claim 10 further comprising a step of administering an immune checkpoint inhibitor.

20. The method of claim 10 wherein the genetically modified virus is administered via subcutaneous or intratumoral injection.

21. The method of claim 1 wherein the co-stimulatory molecule comprises ICAM-1 (CD54), ICOS-L, LFA-3 (CD58), B7.1 (CD80), B7.2 (CD86), or combinations thereof.

22. The method of claim 1 wherein the co-stimulatory molecule comprises 4-1BBL, CD30L, CD40, CD40L, CD48, CD70, CD112, CD155, GITRL, OX40L, and TL1A.

* * * * *

SEQUENCE LISTING

```
<160> NUMBER OF SEQ ID NOS: 1

<210> SEQ ID NO 1
<211> LENGTH: 2082
<212> TYPE: DNA
<213> ORGANISM: artificial
<220> FEATURE:
<223> OTHER INFORMATION: Chimeric protein between EBV LMP1 transmembrane
      domain and murine IPS1 signaling domain
<220> FEATURE:
<221> NAME/KEY: misc_feature
<222> LOCATION: (1)..(578)
<223> OTHER INFORMATION: EBV LMP1 transmembrane domain
<220> FEATURE:
<221> NAME/KEY: misc_feature
<222> LOCATION: (579)..(2630)
<223> OTHER INFORMATION: Murine IPS1 signaling domain
```

<400> SEQUENCE: 1

```
atggaacacg accttgagag gggcccaccg ggcccgcgac ggcccctcg aggacccccc      60
ctctcctctt ccataggcct tgctctcctt ctcctgctct tggcgctact gttttggctg    120
tacatcatta tgagtaactg gactggagga gccctccttg tcctctatgc ctttgctctc    180
atgcttgtga ttatcatttt gatcatcttt atcttcagaa gagaccttct ctgtccactt    240
ggagcccttt gtctactcct actgatgatc accctcctgc tcatcgctct tggaatttg    300
cacggacagg cattgtacct tggaattgtg ctgttcatct tcgggtgctt acttgtctta    360
ggtctctgga tctacttatt ggagattctc tggcgacttg gtgccaccat ctggcagctt    420
ttggccttct tcctagcctt cttcctagac atcatcctgc tcattattgc tctctatcta    480
caacaaaact ggtggactct attggttgat ctccttggc cctcctgtt tctggcgatt     540
ttaatctgga tgtattacca tggacaacga atgacatttg ctgaggacaa gacctataag    600
tatatccgag acaaccacag caagttttgc tgtgttgacg ttctggagat cctgccttac    660
ctgtcctgcc tcacagctag tgaccaggat cgactgcggg cttcctacag gcagatcggg    720
aaccgggaca cactctgggg actcttcaat aatctccagc gccggcctgg ctgggtggag    780
gtcttcatcc gggcactgca gatctgtgag ctgcctgggc tggctgatca agtgactcga    840
gtttatcaga gctacctgcc tccggggacc tcactccgct ccctagagcc actgcagtta    900
ccagactttc ctgctgcggt ttctggaccc tctgcatttg cgccaggtca caacatccct    960
gaccatggct tacgagagac accaagttgc cccaagcctg tccaggacac ccagccacca   1020
gagtccccag tagagaattc agagcaactc ctccagacca actccggggc cgtcgcgagg   1080
atgtctggtg gctctttgat accctctcct aaccagcagg ctctcagccc tcagccctcc   1140
agagagcatc aagagcaaga accagaactg ggtggcgccc acgcagcaaa tgttgcctct   1200
gttcccatag caacctatgg acctgtgtct ccaaccgttt ccttccagcc ccttccacgt   1260
actgccctga ggacaaaacct cttgtctggg gtcacagtat cagccctatc tgctgatacc   1320
tctttgtcct cctcgtccac tggatcagct tttgcaaagg gagctggtga ccaggccaaa   1380
gctgccacct gtttcagtac tacactcacc aattctgtga ctaccagctc agtgccttct   1440
cccagattgg tcccagtaaa aaccatgtct tccaagttgc ccctcagttc aaagtccact   1500
gctgcgatga cgtctactgt gctcaccaat acagcgccat caaaattacc cagcaactca   1560
gtgtatgcgg gcacagtgcc atccagagtg cctgctagtg tggccaaagc acctgccaac   1620
acaataccac tgagaggaa cagcaagcaa gccaaggaga ccccggaggg tccagcaacc   1680
aaagtcacca ctggaggcaa ccagactgga ccaaatagca gtatcaggag cttgcactct   1740
ggaccagaga tgagcaagcc aggtgtgctg gtatcccagt tggacgagcc attctcagcc   1800
tgctctgtgg accttgccat tagccctagc agctccttgg tctcagaacc caaccatggt   1860
ccagaggaga atgagtattc gtcctttaga atccaggtag acgaaagccc cagtgctgat   1920
ctattaggaa gccctgagcc actagccacc cagcagcccc aagaagagga agaacattgt   1980
gccagttcaa tgccctgggc taagtggctt ggggccacca gtgcactctt ggctgtattc   2040
ctggcagtga tgctgtaccg tagtaggcgc ctggcccagt ga                      2082
```